United States Patent [19]

Rabilloud et al.

[11] 4,310,699

[45] Jan. 12, 1982

[54] PROCESS FOR SYNTHESIZING BIS (PHENYLGLYOXYLOYL)BENZENES USABLE FOR MANUFACTURING POLYPHENYLQUINOXALINE RESINS

[75] Inventors: Guy Rabilloud, Grenoble; Bernard Sillion, Lyons, both of France

[73] Assignee: Institut Francais du Petrole, Rueil-Malmaison, France

[21] Appl. No.: 152,895

[22] Filed: May 23, 1980

[30] Foreign Application Priority Data

May 23, 1979 [FR] France .............................. 79 13424

[51] Int. Cl.$^3$ ...................... C07C 45/29; C07C 45/45
[52] U.S. Cl. ................................... 568/315; 568/312
[58] Field of Search .............................. 568/315, 312

[56] References Cited

U.S. PATENT DOCUMENTS 4,024,067  5/1977  Paciorek et al. .................... 568/315

OTHER PUBLICATIONS

Oppenheimer, Berichte, vol. 119, pp. 1814–1818 (1886).
Kulbrick et al., J.A.C.S., vol 93(5), pp. 1214–1222 (1971).
Ogata et al., The Chem. of the Carbonyl Group, pp. 20–32 (1970).
Kratzer et al., J. Org. Chem., vol. 41, pp. 2230–2234 (1976).

Primary Examiner—Natalie Trousof
Assistant Examiner—James H. Reamer
Attorney, Agent, or Firm—Millen & White

[57] ABSTRACT

Bis (phenylglyoxyloyl) benzenes are manufactured by a method comprising the reaction of terephthalic or isophthalic aldehyde first with a low proportion of an alkali metal cyanide in a solvent, and then with benzaldehyde; the resultant product is oxidized to the desired bis (phenylglyoxyloyl) benzene.

11 Claims, No Drawings

PROCESS FOR SYNTHESIZING BIS (PHENYLGLYOXYLOYL)BENZENES USABLE FOR MANUFACTURING POLYPHENYLQUINOXALINE RESINS

BACKGROUND OF THE INVENTION

The present invention concerns an improved process for manufacturing 1,4-bis (phenylglyoxyloyl) benzene and 1,3-bis (phenylglyoxyloyl) benzene, which constitute monomers for the manufacture of polyphenylquinoxaline resins.

It is known, in the present state of the art, that the polyphenylquinoxaline resins have exceptional properties of heat stability and resistance to oxidation and to chemical agents, but that an extended use thereof is limited by the excessive cost of the starting monomers, particularly the aromatic bis-α-diketones. The manufacture of these compounds is effectively based on the use of rare and expensive reactants and requires many intermediary steps.

It is also known that the best way to obtain the aromatic α-diketones is to oxidize the corresponding α-keto alcohols, called benzoins. As a rule, benzoins are prepared by condensing one or more aromatic aldehydes in the presence of an alkali metal cyanide, used in an amount far lower than the stoichiometric amount. It has however been stated recently (Kratzer and coll., J. Org. Chem. 41, (1976), 2230) that the mixed benzoinic condensation of terephthalaldehyde with benzaldehyde does not yield the expected bis-benzoin. This compound could only be obtained by first preparing the bis-bisulfitic addition product of terephthalic aldehyde, then reacting it with potassium cyanide in a molar proportion of two, to synthesize the terephthalic bis-cyanohydrin, and finally condensing the latter with a large excess of benzaldehyde. It appears that this method has the disadvantage, as compared with the benzoinic condensation, to make use of potassium cyanide in large amount and to necessitate several distinct reaction steps.

DETAILED DISCUSSION

It has been found, and this is an object of the present invention, that in certain well specified conditions, it is possible to effect a reaction of mixed benzoinic condensation between benzaldehyde, on the one hand, and the terephthalic and isophthalic aldehydes, on the other hand. It has also been found that, in these conditions, the purity of the resultant bis-benzoins is higher than 99% and that they need not be purified before oxidation to the corresponding bis-α-diketones. The latter compounds have then directly the so-called "for polymers" purity grade, i.e. higher than 99%

According to the process of the invention, the bis-benzoin of the formula

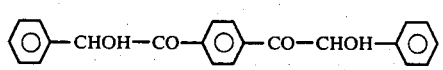   (1)

or of the formula

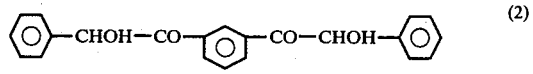   (2)

is first prepared.

Successive operations, generally defined as follows, are conducted:

(a) terephthalic or isophthalic aldehyde is reacted with alkali metal cyanide in a lower proportion than the stoichiometric proportion of 2 moles per mole of tere- (or iso-) phthalic aldehyde, in a solvent able to dissolve the tere-(or iso-) phthalic aldehyde and the alkali metal cyanide, but wherein the desired bis-benzoin is not soluble;

(b) the resultant reaction mixture is reacted with benzaldehyde in excess over the stoichiometrical proportion of 2 moles per mole of tere-(or iso-) phthalic aldehyde (usually 3.5 to 6 moles), said step (b) being conducted at a temperature close to room temperature, for example about from 0° to 30° C.; then (c) the reaction mixture is heated to a temperature of 50° to 150° C., usually at the reflux temperature of the solvent.

According to this method, the bis-benzoin may be obtained with a high yield and a high degree of purity.

To illustrate the importance of the choice of the operating conditions, the mechanism of the mixed benzoinic condensation is described by the following reaction sequence:

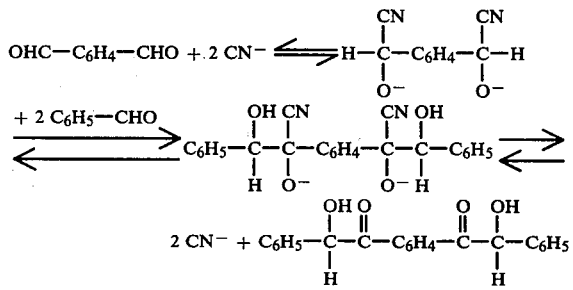

As the alkali metal cyanide is present in the medium in an amount far lower than the proportion of 2 moles per mole of aromatic dialdehyde, the yield to bis-benzoin is the higher as the auto-condensation of benzaldehyde is reduced to a minimum, said auto-condensation yielding ordinary benzoin:

The auto-condensation of the dialdehyde must also be avoided, said auto-condensation yielding polybenzoins of the type:

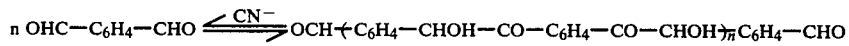

These reactions and other secondary reactions have the result that, under the usual conditions, the mixed benzoinic condensation of benzaldehyde with terephthaldehyde or isophthaldehyde yields mainly tars and little bis-benzoin.

Conversely, the operating conditions of the invention allow the reaction of synthesis of the bis-benzoin to take place with very high yields. Although the yield depends partly on the amount of alkali metal cyanide supplied, it has been observed that it is possible to obtain at least 80% of pure bis-benzoin with only 15 to 20% of the stoichiometrical amount of cyanide. When using 30 to 50% by mole of cyanide, as usually disclosed for such reactions, the yield to bis-benzoin may attain 95% or more.

As a rule, there will thus be used a proportion of alkali metal cyanide of 0.3 to 1 mole per mole of tere-(or iso-) phthalic aldehyde.

In addition, it has been found that, with the same amount of cyanide, the yield to bis-benzoin can be up to twice as large when the reaction is effected in a solvent able to dissolve all the starting reactants but having poor solvent power for the reaction product. As a matter of fact, the benzoinic condensation is usually a reversible reaction and the fact of eliminating by settling, in the course of the reaction, the desired product displaces the equilibrium in the desired direction.

When the reaction is effected without solvent, the excess of benzaldehyde plays at least in part this role with respect to the aromatic dialdehyde. The alkali metal cyanides have however a poor solubility in benzaldehyde. If the cyanide is added in aqueous solution, the reaction medium is formed of two immiscible phases. The transfer of the cyanide from the aqueous phase to the organic phase may be accelerated by addition of a phase transfer agent such as, for example, a quaternary ammonium salt or a quaternary phosphonium salt. At the end of the reaction, the organic phase appears as a blackish pasty mass wherefrom the bis-benzoin connot be extracted easily.

When the reaction solvent is able to dissolve the aldehydes and not the cyanide, the situation is partially the same as in the above case of a two-phase system, an organic phase containing the aldehydes and an aqueous phase containing the cyanide. The reaction connot be controlled easily in that case, since the transfer of the reactants from one phase to the other must be effected in well specified conditions and the resultant product has not the purity obtained in homogeneous phase.

Among the organic solvents which can be used in the invention, there will be selected those which can dissolve the starting compounds of lower solubility, such as terephthalaldehyde and potassium or sodium cyanide. The primary aliphatic alcohols are the most advantageous solvents, and particularly the lower alcohols, such as, for example, methanol or ethanol, wherein the alkali metal cyanides are reasonably soluble (potassium cyanide is substantially more soluble than sodium cyanide). The lower alcohol comprises generally from 1 to 4 carbon atoms.

Conversely, when effecting the reaction, for example, in solution in aromatic hydrocarbons such as benzene and toluene, the metal cyanide should be added as an aqueous solution and the condensation would yield the bis-benzoin with a substantially lower yield.

According to the invention, there is advantageously used a proportion of organic solvent of 1 to 6 liters per mole of tere-(or iso-) phthalic aldehyde.

The mode of addition of these various reactants is also very important: the method of the invention consists of adding the alkali metal cyanide which, for reasons of solubility, is generally potassium cyanide, to the organic solution of the aromatic dialdehyde. A compound of dark red color forms very quickly, to which benzaldehyde is subsequently added to react with this colored compound. The yield to bis-benzoin is substantially higher in these conditions than when the cyanide is added to a common solution of the two aldehydes.

In all these mixed condensation reactions of a di-functional reactant with a mono-functional reactant it is advantageous to use an excess of the latter to reduce as much as possible the polycondensation of the di-functional compound. To synthesize a bis-benzoin, the stoichiometrical ratio is 2 moles of benzaldehyde per mole of dialdehyde. With an excess of 100%, i.e. 4 moles of benzaldehyde, the polycondensation of the dialdehyde on itself no longer occurs and the reaction product is not contaminated with the benzoin which could result from the auto-condensation of benzaldehyde. A larger excess of benzaldehyde may of course be used, but without substantial increase of the yield to bis-benzoin. Generally from 3.5 to 6 moles of benzaldehyde are used per mole of tere-(or iso-) phthalic aldehyde.

The temperature has also a considerable influence on the yield of the reaction. With the same amount of alkali metal cyanide, the yield to the bis-benzoin is, for example, 30% when the reaction is conducted at the reflux temperature of the solvent. The yield amounts to 65% when the reaction is conducted at room temperature. It may attain 80% or more when, according to the invention, the reaction is conducted first at a temperature close to room temperature, comprised for example between 0° and 30° C., and then at a higher temperature, usually between 50° and 150° C. This second phase is usually conducted at the reflux temperature of the solvent. Further, the appearance of the precipitate of bis-benzoin modifies by heating. Instead of a very fine precipitate, which is excessively difficult to wash and filter, as obtained when the reaction is conducted at room temperature, the heating of the reaction medium yields a precipitate of greater particle size which can be more easily washed and filtered. Advantageously, the first phase (at a temperature close to room temperature) requires from 0.5 to 5 h, and the second phase (at a higher temperature) from 3 to 10 hours.

In the improved process of the invention, a bis-benzoin is obtained with a high yield and a very high degree of purity. The spectroscopic analyses and the techniques of separation by thin layer chromatography or by chromatography in a high performance column do not reveal the presence of any contaminating substance. This means that the crude bis-benzoin has a purity of at least 99%, and therefore needs no further purification.

The second step in the synthesis of the 1,4- and 1,3-bis (phenylglyoxyloyl)benzenes is the oxidation of the corresponding bis-benzoins to bis-$\alpha$-diketones. The conversion to ketone of a secondary alcohol group in $\alpha$-position to a carbonyl group may be effected by known techniques, by means of an oxidizing agent derived, for example, from copper, manganese, chromium, bismuth, lead, selenium, cerium, silver and a great number of other metals. The oxidizing agent may also be nitric acid or nitrogen tetroxide.

Large amounts of bis-$\alpha$-diketones may be advantageously manufactured by oxidation with copper acetate and ammonium nitrate; the resultant products are then of high purity and no further purification is required. They can be used directly to prepare polyphenyl-quinoxaline resins of very high molecular weight.

The invention will be more precisely described in the following specific examples, in which the details are given for illustration and not limitation. In these examples, the yields to bis-benzoin are calculated with respect to the reacted amount of dialdehyde. The purity of the products is determined by chromatography, mass spectrography and nuclear magnetic resonance.

The examples 1 to 3, 9 and 14 illustrate the invention. The other examples are destined to illustrate the results obtained with operating conditions which differ from the optimum conditions defined in the invention.

EXAMPLE 1

(a) 15 liters of methanol and 625 g (4.66 mol) of terephthalaldehyde are introduced into a 20 liter reactor equipped with a stirrer and a reflux cooler. The mixture is stirred up to dissolution of the dialdehyde. 100 g (1.54 mol) of potassium cyanide is then added, i.e. about 16% of the stoichiometrical amount. The cyanide dissolves quickly and the medium takes a dark red color. 2000 g (18.9 mol) of benzaldehyde are then added. The mixture is stirred for 1 hour at room temperature. It is then heated for 5 hours at the reflux temperature of methanol (about 70° C.). After cooling to room temperature, the formed precipitate of creamy white color is isolated by filtration, washed with water to remove the cyanide and dried under reduced pressure. When effecting five identical operations, the bis-benzoin yield varies from 1272 g (79%) to 1340 g (83%). The elemental analysis and the spectroscopic (infra-red, ultra-violet, NMR and mass) analyses show that the resultant compound has the formula of the expected bis-benzoin. The analysis by thin layer chromatography and by chromatography in a high performance column show that the resultant product has a purity of at least 99%.

(b) The oxidation of the resultant bis-benzoin to 1,4-bis (phenylglyoxyloyl) benzene is effected according to the following process:

10 liters of acetic acid, 500 g of bis-benzoin, 320 g of ammonium nitrate, 6.5 g of copper acetate di-hydrate and then 7 liters of aqueous acetic acid of 50% water content by volume are successively introduced into a 20 liter-reactor provided with a mechanical stirrer, a reflux condenser and an inert gas circulation. The mixture is heated at reflux (110° C.) for 30 hours and then cooled to 0°-5° C. A yellow crystalline precipitate forms, which is isolated by filtration and washed three times with 2 liters of water. It is then dried at 100° C. for several hours.

The mother liquors recovered after filtration of the precipitate are fed back to the reactor and charged again with 500 g of bis-benzoin and 320 g of ammonium nitrate. The oxidation of this second sample is effected in the conditions described above.

This operation is repeated twice with charges of 500 g of bis-benzoin and 320 g of ammonium nitrate.

The four samples of 1,4-bis (phenylglyoxyloyl) benzene thus prepared have respective weights of 342 g, 450 g, 458 g and 460 g. The tetraketone yield is approximately 70% for the first preparation. It ranges then between 91 and 93% for the three other runs.

The resultant compound has a melting temperature of 127° C. and the different analyses conform to the expected structure. The chromatographic analysis shows the presence of a single compound whose purity is higher than 99%. A series of three successive re-crystallizations in ethanol does not modify the physical and spectroscopic properties of the crude product of the reaction. The latter is thus directly usable for preparing polyphenylquinoxalines of high molecular weight.

EXAMPLE 2

The benzoinic condensation of terephthalaldehyde (625 g) with benzaldehyde (2000 g) is effected in conditions strictly identical to those of example 1, while using 300 g of potassium cyanide, which represents 50% of the stoichiometrical proportion. The yield of pure bis-benzoin is 1516 g (94%). This product, when oxidized, yields 90% of very pure 1,4-bis (phenylglyoxyloyl) benzene. The tetraketone yield thus averages 85% with respect to the reacted terephthalic aldehyde.

EXAMPLE 3

A benzoinic condensation is effected between isophthalaldehyde and benzaldehyde in the conditions of example 1. The higher solubility of this dialdehyde results in an increase of the amount reacted in 15 liters of methanol to 1340 g (10 mol) for isophthalic dialdehyde, 260 g (4 mol) for potassium cyanide (20% of the stoichiometrical amount) and 4240 g (40 mol) for benzaldehyde. This operation yields 2770 g (80%) of the expected bis-benzoin.

Three samples of about 920 g of the resultant compound are oxidized in the conditions of example 1. The yield of 1,3-bis (phenylglyoxyloyl) benzene is 85% with respect to the bis-benzoin and about 68% with respect to the starting isophthalaldehyde.

EXAMPLES 4 TO 12

These examples have for object to show the influence of the different factors (amount of cyanide, volume of solvent, temperature and reaction time) on the yield of bis-benzoin and the purity thereof.

The experiments are effected by dissolving 80 g (0.597 mol) of terephthaladehyde and 250 g (2.36 mol) of benzaldehyde in methanol. The amount of potassium cyanide indicated in Table I is then added, and the reaction is performed under the various conditions of temperature and time reported in said Table.

TABLE I

| EXAMPLE No. | K CN Weight (g) | % Theor. | SOLVENT Vol. (ml) | TIME (h) | TEMP. (°C.) | BIS-BENZOIN YIELD Weight (g) | % |
|---|---|---|---|---|---|---|---|
| 4 | 2.5 | 3 | 400 | 4 | 20 | 0 | 0 |
| 5 | 8.8 | 11 | 400 | 4 | 20 | 38 | 18.4 |
| 6 | 12.5 | 16 | 400 | 4 | 20 | 97 | 47 |
| 7 | 12.5 | 16 | 2000 | 4 | 20 | 101 | 49 |
| 8 | 12.5 | 16 | 2000 | 5 | 70 | 54 | 26 |
| 9 | 12.5 | 16 | 2000 | 0.5 +4.5 | 20 70 | 133 | 64.4 |
| 10 | 25 | 32 | 2000 | 4 | 20 | 115 | 55.7 |
| 11 | 25 | 32 | 2000 | 6 | 70 | 90 | 44 |
| 12 | 35 | 45 | 2000 | 4 | 20 | 129 | 62.5 |

The solvent volume has an influence on the purity of the product, which is at least 99% in examples 7 to 12 (2 l. of solvent) and only 95% in examples 5 and 6 (0.4 liter of solvent).

The examples 4, 5, 7, 10 and 12 show that the bis-benzoin yield increases with the amount of cyanide.

The comparison of the example 7 and 8, on the one hand, and 10 and 11, on the other hand, shows that the yield is higher when the reaction is conducted at 20° C. than when performed entirely at 70° C.

A comparison of examples 7 and 9 shows that the yield increases when the reaction is effected first at 20° C. and then at 70° C.

EXAMPLE 13 TO 16

These examples, performed according to the method of example 1, show the influence of an excess of benzaldehyde on the bis-benzoin yield.

The experiments are performed by dissolving 80 g of terephthalaldehyde, 12.5 g of KCN and the amount of benzaldehyde indicated in Table II into 2 liters of methanol. The reaction is conducted at 20° C. for 1 hour and then at 70° C. for 6 hours.

TABLE II

| EXAMPLE No. | BENZALDEHYDE Weight (g) | % Theor. | BIS-BENZOIN YIELD % |
|---|---|---|---|
| 13 | 127 | 100 | 25 |
| 14 | 254 | 200 | 80 |
| 15 | 635 | 500 | 45 |
| 16 | 1270 | 1000 | 15 |

A comparison of these examples shows that the optimum proportion of benzaldehyde is about twice the stoichiometrical proportion and that a far larger excess is not advantageous.

EXAMPLE 17

This comparison example is destined to show the results obtained when the reaction is performed without solvent in a two-phase system.

In a reactor equipped with a high speed stirrer of the "ultraturax" type, there is introduced 80 g of terephthalaldehyde, 250 ml of benzaldehyde, 1000 ml of water, 22 g of potassium cyanide and 65 g of tricaprylammonium chloride. The mixture is stirred efficiently for 20 minutes at room temperature. The organic phase is washed several times with boiling ethanol and then filtered and dried. The yield of 90% pure bis-benzoin is only 50%.

EXAMPLE 18

This comparison example shows the use of an organic solvent in which the potassium cyanide is not soluble.

To an efficiently stirred solution of terephthalaldehyde (80 g) and benzaldehyde (250 g) in 2 liters of benzene, there is added a solution of potassium cyanide (12.5 g) in 200 ml of water and then, dropwise, a solution of 40 g of tricaprylmethylammonium chloride in 200 ml of water. After 5 hours of stirring, the organic phase is decanted. Benzene is separated by filtration from the suspended solid mass. The latter is washed three times with boiling ethanol; the yield of 92% pure bis-benzoin is only 35%.

What is claimed is:

1. A process for preparing a bis-benzoin having the formula

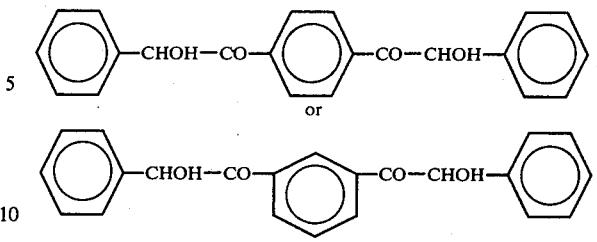

said process comprising the steps of:
(a) reacting terephthalic or isophthalic aldehyde with an alkali metal cyanide in a molar ratio of cyanide to aldehyde of from 0.3:1 to 1:1 the reaction being effected in a $C_{1-4}$ monoalcohol solvent, the amount of solvent being from 1 to 6 liters per mole of said aldehyde;
(b) adding to the resultant reaction mixture from step (a) from 3.5 to 6 moles of benzaldehyde per mole of terephthalic or isophthalic aldehyde used in step (a), at a temperature of from 0° to 30° C.; and
(c) heating the resultant reaction mixture from step (b) at a temperature of from 50° to 150° C., and recovering the resultant precipitated bis-benzoin; whereby the recovered bis-benzoin is produced in high yield and high purity.

2. A process according to claim 1, wherein said $C_{1-4}$ monoalcohol is methanol.

3. A process according to claim 1, wherein in step (a), the molar ratio of cyanide to aldehyde is from 0.6:1 to 1:1.

4. In a process for preparing 1,4-bis(phenylglyoxyloyl)benzene or 1,3-bis(phenylglyoxyloyl)benzene, which comprises preparing a bis-benzoin of the formula

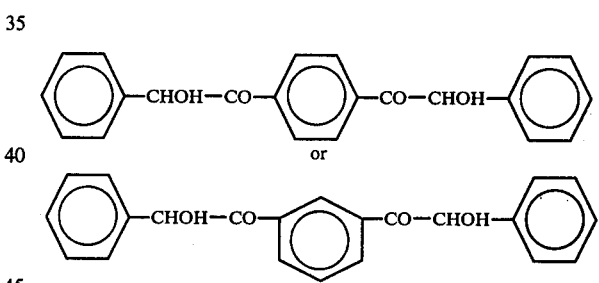

and oxidizing the bis-benzoin to the corresponding bis(-phenylglyoxyloyl)benzene,
the improvement which comprises preparing said bis-benzoin by the process of claim 1.

5. A process according to claim 4, wherein the alkali metal cyanide is potassium cyanide.

6. A process according to claim 4, wherein the operating time of step (b), effected at 0°–30° C., is from 0.5 to 5 hours, and the operating time of step (c), effected at 50°–150° C., is from 3 to 10 hours.

7. A process according to claim 4, wherein said $C_{1-4}$ monoalcohol is methanol.

8. A process according to claim 4, wherein in step (a), the molar ratio of cyanide to aldehyde is from 0.6:1 to 1:1.

9. A process according to claim 1, wherein the alkali metal cyanide is potassium cyanide.

10. A process according to claim 1, wherein the operating time of step (b), effected at 0°–30° C., is from 0.5 to 5 hours, and the operating time of step (c), effected at 50°–150° C., is from 3 to 10 hours.

11. A process according to claim 4, wherein the said bis-benzoin is oxidized with an oxidizing agent comprising copper acetate and ammonium nitrate.

* * * * *